(12) United States Patent
Smith

(10) Patent No.: US 6,986,786 B1
(45) Date of Patent: Jan. 17, 2006

(54) ENDOVASCULAR PROSTETHIC DEVICES HAVING HOOK AND LOOP STRUCTURES

(75) Inventor: John K. Smith, Medford, MA (US)

(73) Assignee: SCIMED Life Systerms, Inc., Maple Grove, MN (US)

( * ) Notice: Subject to any disclaimer, the term of this patent is extended or adjusted under 35 U.S.C. 154(b) by 699 days.

(21) Appl. No.: 09/660,078

(22) Filed: Sep. 11, 2000

(51) Int. Cl.
  *A61F 2/06* (2006.01)

(52) U.S. Cl. .................. 623/1.36; 623/1.13; 623/1.16; 623/1.35; 623/1.51

(58) Field of Classification Search ............... 623/1.13, 623/1.15, 1.16, 1.27, 1.35, 1.36, 1.51, 1.3; 128/898; 606/194
See application file for complete search history.

(56) References Cited

U.S. PATENT DOCUMENTS

| | | | |
|---|---|---|---|
| 3,577,607 A | | 5/1971 | Ikoma et al. |
| 3,594,873 A | | 7/1971 | Hockmeyer et al. |
| 3,748,701 A | | 7/1973 | De Mestral |
| 3,943,981 A | | 3/1976 | De Brabander |
| 5,084,065 A | * | 1/1992 | Weldon et al. .............. 623/1.44 |
| 5,254,133 A | * | 10/1993 | Seid ............................ 606/215 |
| 5,383,897 A | * | 1/1995 | Wholey ....................... 606/213 |
| 5,683,450 A | | 11/1997 | Goicoechea et al. |
| 5,716,365 A | | 2/1998 | Goicoechea et al. |
| 5,718,724 A | | 2/1998 | Goicoechea et al. |
| 5,723,003 A | | 3/1998 | Winston et al. |
| 5,776,180 A | | 7/1998 | Goicoechea et al. |
| 5,843,170 A | | 12/1998 | Ahn |
| 5,916,263 A | | 6/1999 | Goicoechea et al. |
| 5,938,696 A | | 8/1999 | Goicoechea et al. |
| 6,035,856 A | * | 3/2000 | LaFontaine et al. ......... 128/898 |
| 6,051,020 A | | 4/2000 | Goicoechea et al. |
| 6,344,056 B1 | * | 2/2002 | Dehdashtian ............... 623/1.35 |
| 6,390,098 B1 | * | 5/2002 | LaFontaine et al. ......... 128/898 |
| 6,478,817 B2 | * | 11/2002 | Schmitt et al. ............. 623/1.35 |
| 6,485,524 B2 | * | 11/2002 | Strecker ..................... 623/1.15 |
| 6,576,009 B2 | * | 6/2003 | Ryan et al. ................. 623/1.35 |
| 2003/0120332 A1 | * | 6/2003 | Hartley ....................... 623/1.13 |

FOREIGN PATENT DOCUMENTS

DE  19703482 A  8/1998

\* cited by examiner

*Primary Examiner*—Henry Bennett
*Assistant Examiner*—Andrea M. Ragonese
(74) *Attorney, Agent, or Firm*—Hoffmann & Baron, LLP (57) ABSTRACT

The prostheses include an endovascular member in need of repair and a patch therefore, as well as prostheses including two or more endovascular members, such as stent-grafts, which may be assembled in situ. Components of the prostheses are held together in substantially fluid tight engagement as the result of hook and loop structures which are present on the members. The hooks engage the loops to secure the components to one another. As a result, the present invention is particularly useful for the in situ repair of damaged prostheses and for the in situ assembly of bifurcated endovascular prostheses, particularly for the treatment of abdominal aortic aneurysms.

7 Claims, 4 Drawing Sheets

ENDOVASCULAR PROSTETHIC DEVICES HAVING HOOK AND LOOP STRUCTURES

FIELD OF THE INVENTION

The present invention is directed to multiple-component endovascular prostheses having textile structures of mating hooks and loops, which maintain the components of the prostheses in substantially fluid tight engagement with one another. More particularly, the present invention is directed to bifurcated endovascular prostheses comprised of two or more stent-graft components having textile structures of hooks and loops which may be assembled in situ for use in bifurcated blood vessels, such as the infrarenal portion of the mammalian aortic artery where it bifurcates to the common iliac arteries.

BACKGROUND OF THE INVENTION

An abdominal aortic aneurysm ("AAA") is an abnormal dilation of the arterial wall of the aorta in the region of the aorta that passes through the abdominal cavity. The condition most commonly results from atherosclerotic disease. Abdominal aortic aneurysms are typically dissecting aneurysms, which are aneurysms that are formed when there is a tear or fissure in the arterial lining or wall through which blood is forced and eventually clots, forming a thrombosis which swells and weakens the vessel. Abdominal aortic aneurysms typically do not cause pain and are easily detected by physical examination. The aneurysm may rupture if it is not detected and treated, causing massive hemorrhaging which is likely to be fatal to the patient.

Treatment of AAAs typically comprises some form of arterial reconstructive surgery, commonly referred to as a "triple-A" procedure. One such method is bypass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a thin-walled biocompatible material. Nylons and synthetic fibers, such as DACRON® and TEFLON®, are typically used in the construction of such grafts. When performed prior to rupture of an aneurysm, the mortality rate is less than 5%.

Many patients experiencing such AAAs, however, are over 65 years of age and often have other chronic illnesses which increase the risk of perioperative or post-operative complications. Thus, such patients are not ideal candidates for triple-A procedures. Further, this procedure is generally not performed successfully once an aneurysm has ruptured due to the extensiveness of the surgery and the time required to prepare a patient for surgery. The mortality rate for patient experiencing such ruptured aneurysms is over 65%.

As a result of the aforementioned disadvantages to conventional surgical methods, minimally invasive techniques have been developed for the repair of AAAs. Such methods involve placement of a stent-graft at the site of the aneurysm by a catheter, known as an introducer, which serves as a deployment device. The stent-graft and its deployment system are typically introduced into the blood stream percutaneously and negotiated by means of a guidewire to the site of the aneurysm where the stent is caused to be radially expanded. Such procedures are desirable as they can be performed using local anesthesia and do not expose the patient to many of the same risks associated with triple-A procedures.

In such minimally invasive repair procedures, the bifurcated structure of the abdominal aortic arch necessitates the use of a uniquely-structured bifurcated stent-graft. Typically, aneurysms, occlusions or stenoses will occur at the location where the aortic arch bifurcates into the iliac arteries and may also occur at the iliac arteries. The in situ positioning of stent-grafts in this area is more difficult than the positioning of such devices in the lumen of non-bifurcated vessels. As both limbs of a bifurcated stent-graft are inserted and advanced through a single branch of the femoral arterial system, one of the limbs of the stent-graft must ultimately be pulled or drawn into the contralateral branch so that the stent-graft is suitably positioned across both the aortic aneurysm and the associated common iliac aneurysms to supply circulation to each of the lower limbs.

Bifurcated stent-grafts are frequently too bulky to advance through a single iliac artery, particularly in view of the fact that the limb for the contralateral branch of the stent-graft must be inserted together with the limb of the ipsilateral branch. Additionally, care must be taken to not twist or kink the stent-graft as it is placed in the contralateral artery. The caudal portion of the graft must not stretch across the mouth of the internal iliac artery which would result in inadvertent occlusion of that artery. The procedure of drawing one limb of the stent-graft from one femoral artery to the contralateral femoral artery requires placement of a cross-femoral catheter using a closable wire basket prior to insertion of the stent-graft.

This procedure requires significant and skillful wire catheter manipulation, frequently within the aneurysmal cavity. As such, care must be taken to avoid disturbing or dislodging thrombic or embolic material from within the aneurysmal sac. Additional factors such as the severe tortuosity of the iliac arteries and the marked angulation of the aortoiliac junction resulting form the tendency of the abdominal aortic artery to extend caudally during aneurysm formation combine to make deployment of endoluminal bifurcated grafts time consuming and at increased risk of procedural complications and failure.

To overcome the aforementioned risks associated with the use of one-piece stent-grafts in the repair of aneurysms occurring in bifurcated vessels, two-piece stent-grafts have been developed which may be assembled in situ. Examples of such two-piece stent-grafts are disclosed in U.S. Pat. Nos. 6,051,020, 5,938,696, and 5,916,263, all to Goicoechea et al., wherein a first stent-graft is positioned within one branch of the femoral arterial system and a second stent-graft is subsequently positioned with a contralateral branch thereof and attached to the first component. Attachment of the components typically occurs by overlapping sections of the components which are held together by friction forces.

Additionally, prosthetic devices used in the repair of AAAs have been found to be extremely vulnerable to wearing, particularly as a result of the tortuous nature of vessel lumens. Such wearing necessitates the repair of these devices, requiring additional surgical procedures which may include replacement of the device. Consequently, there is a continuing need for the development of stent grafts and techniques useful for the repair of AAAs and for the repair of AAA devices.

SUMMARY OF THE INVENTION

Accordingly, the present invention is directed to an improved endovascular prosthesis and methods of repairing aneurysms, occlusions, and stenoses using such a prosthesis, wherein the prosthesis includes stent-graft components having hook and loop structures which permit the in situ assembly of the prosthesis while maintaining the components thereof in substantially fluid tight engagement with one another.

Additionally, the present invention is directed to an endovascular prosthesis and method of repairing the same, wherein the prosthesis includes a patch for the repair of a worn section of an endovascular member. The member and patch have hook and loop structures cooperative with one another such that the patch may be introduced endovascularly and applied to the stent-graft in situ, thereby forming a fluid-tight seal over the worn area. Endovascular introduction of the patch permits repair of the damaged endovascular member in an effective and minimally-invasive manner.

In one aspect, the present invention is directed to an endovascular prosthesis which includes: (1) an endovascular member having a structure comprising one of a hook structure and a loop structure; and (2) a patch for placement against the endovascular member which has a structure comprising the other of the hook structure and the loop structure. The hook and loop structures are matingly engageable so as to maintain the patch in substantially fluid tight engagement with the endovascular member. Further, the endovascular member may be a graft, stent or stent-graft and the hook and loop structures may be comprised of textile materials. The loops may also be formed from polypropylene, polyethylene teraphthalate, polyurethane, a copolyester elastomer, or nylon.

In a method aspect, the present invention is directed to a method of repairing a damaged area of an endovascular prosthesis having a hook or loop structure and which is positioned within a body lumen. The method includes the step of attaching in situ a patch to an endovascular member, wherein the patch has a hook or loop structure cooperative with a hook or loop structure of the endovascular member which maintains the patch in substantially fluid tight communication with the endovascular member. The patch may be delivered to the endovascular member through a body lumen containing the endovascular member, such as through the use of a balloon catheter. Further, the patch may be attached to the endovascular member by expanding a balloon affixed to a catheter which causes the hook or loop structure of the patch to engage the other of the hook or loop structure of the endovascular member.

In another aspect, the present invention is directed to a multi-component endovascular prosthesis which includes: (1) a first prosthetic component which has a structure comprising one of a hook structure and a loop structure; and (2) a second prosthetic component which has a structure comprising the other of the hook structure and the loop structure. The hook structure and the loop structures are matingly engageable so as to maintain the first prosthetic component in substantially fluid tight engagement with the second prosthetic component.

In another aspect, the present invention is directed to a bifurcated endovascular prosthesis which includes: (1) a main prosthetic component which has a structure comprising one of a hook structure and a loop structure; and (2) a branch prosthetic component which has a structure comprising the other of the hook structure and the loop structure. The hook and loop structures are matingly engageable so as to maintain the main prosthetic component in substantially fluid tight engagement with the branch prosthetic component.

In a further method aspect, the present invention is directed to a method for the assembly of an endovascular prosthesis which is implantable within a body lumen, which includes the steps of: (1) providing a first prosthetic component having one of a hook or loop structure; (2) providing a second prosthetic component having the other of the hook or loop structure; and (3) engaging in situ the hook structure or the loop structure of the first prosthetic component with the other of the hook structure or the loop structure of the second prosthetic component so as to maintain the first prosthetic component in substantially fluid tight engagement with the second prosthetic component. The endovascular prosthesis is useful for the treatment of aneurysms, particularly abdominal aortic aneurysms.

DETAILED DESCRIPTION OF THE INVENTION

The present invention is directed to a multi-component endovascular prosthesis which includes multiple stent components covered with grafts, the endovascular prosthesis being hereinafter referred to as a prosthesis. The components have hook and loop structures which are matingly engageable, i.e. complementary, so as to maintain them in substantially fluid tight engagement with one another. The hook and loop textile structures may be formed from any biocompatible material such as, for example, material sold under the tradename Velcro® and described in U.S. Pat. No. 3,748,701 to De Mestral, U.S. Pat. No. 3,943,981 to De Brabander, U.S. Pat. No. 3,594,873 to Hockmeyer et al., and U.S. Pat. No. 3,577,607 to Ikoma et al., all incorporated by reference herein.

The present invention is well-suited for the repair of aneurysms, occlusions, stenoses, and other blood vessel conditions typically resulting from atherosclerotic disease and repaired using a stent, graft, or stent-graft prosthesis. Additionally, dissections of blood vessels, such as those due to blunt trauma to, for example, the chest, are also well-suited for repair by devices of the present invention. A prosthesis of the present invention is capable of being introduced into the body as multiple components and then assembled in situ. Such assembly allows for precise positioning of the prosthesis and avoids complications, such as inadvertent occlusions and the dislodging of thrombic or embolic material, associated with the use of one-piece stent-grafts, particularly in bifurcated vessels.

Assembly of the components is accomplished by engaging cooperative hook and loop structures of the components. The components are overlapped sufficiently to permit the hook and loop structures to engage one another when the components are placed in a face-to-face arrangement, forming a substantially fluid-tight seal therebetween. Any number of components can be assembled in this manner, thus permitting the surgeon a great deal of flexibility in the manner in which the prosthesis will be positioned within the lumen of blood vessels. By assembling the components in situ, smaller members are drawn through the lumen than as with one-piece prosthetic devices. Additionally, twisting of the prosthesis in the lumen in order to properly position it is avoided, thereby decreasing the risk of incidental damage to the vessel and thrombi release into the vessel stream.

The present invention is also well suited to the in situ repair of a damaged endovascular member (e.g., a stent graft) which, for example, has become worn due to tortuous blood flow. Such repair may occur by patching or replacing a worn area of the member. The patch used in the repair has a hook or loop structure which is complementary to a hook or loop structure of the member in need of repair. As such, the repair material cooperatively engages the material of the member resulting in a substantially fluid-tight seal therebetween, thereby permitting the effective and complete repair of the damaged area using minimally invasive techniques.

A stent useful in the present invention is an intraluminal stent having any number of configurations and may include attachment hooks to assist in attaching the stent to the aortic wall after the stent has been expanded. Other types of stents are useful in the present invention, including expandable stents without hooks or self-expanding stents with or without attachment hooks. Stents useful in the present invention can be made from metals or polymers and have numerous configurations.

The present invention is suited for use with conventional stents, grafts, and stent-graft devices, and therefore is suitable for use in all known vascular applications employing such devices. As the hook and loop structures of the mating parts provides a strong and substantially fluid-tight seal therebetween, the present invention is well suited to use in any vessel where a prostheses are susceptible to wear (e.g., where extreme tortuosity is encountered) and where it is advantageous to assemble such prostheses in situ.

Figure 1:
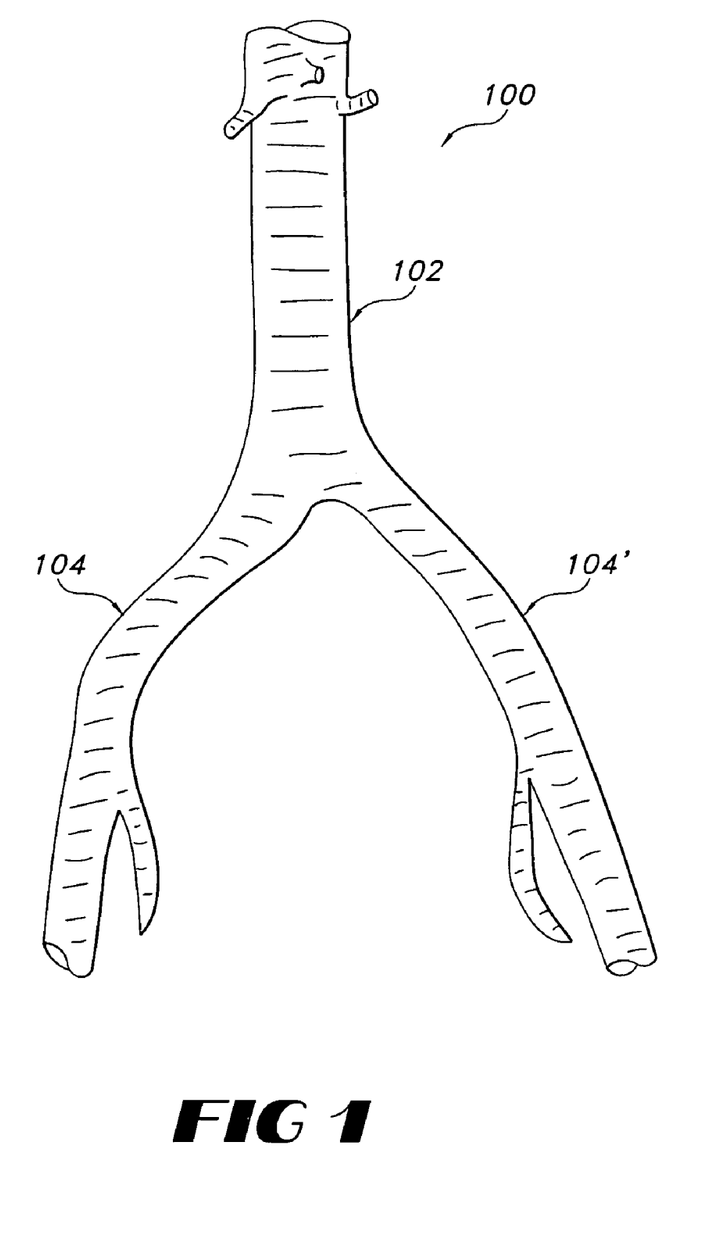
FIG. 1 is a diagrammatic view of the abdominal aortic arch of the human vascular system depicting the descending aorta and the right and left common iliac arteries.
Figure 2:
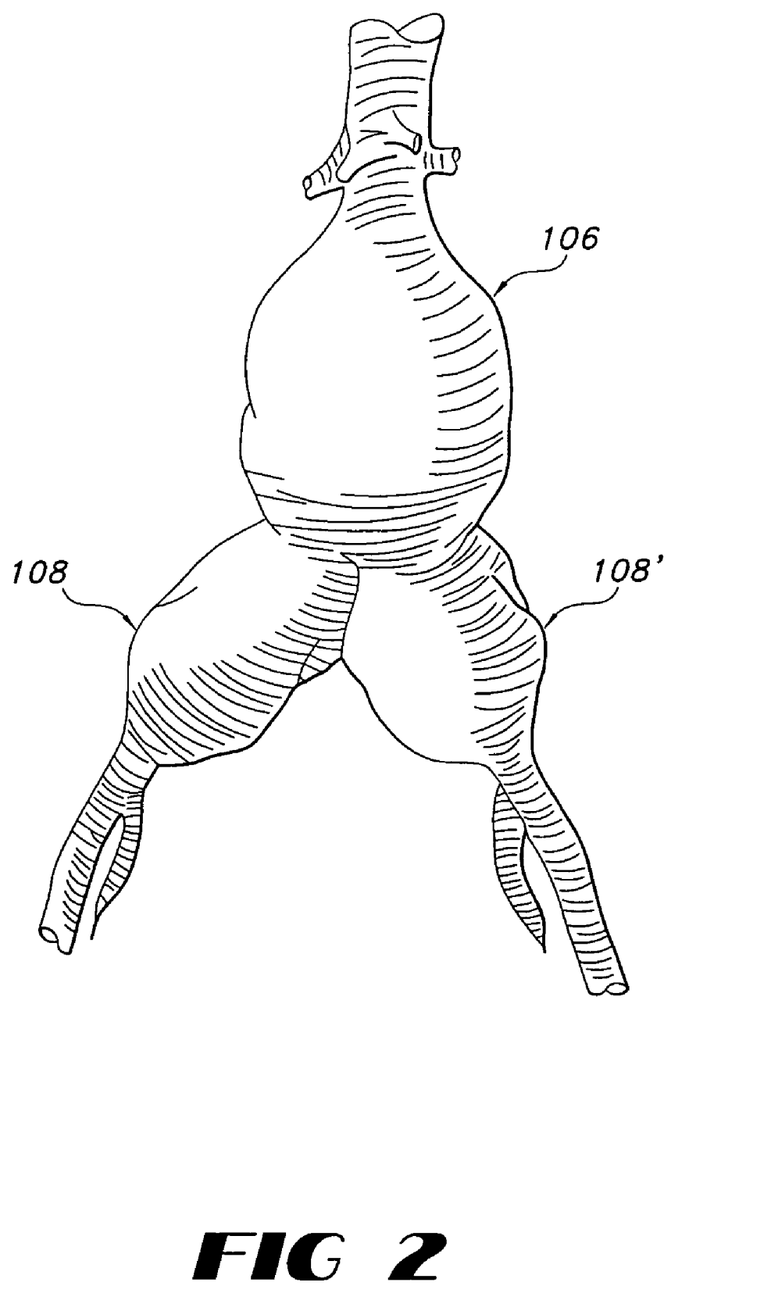
FIG. 2 is a diagrammatic view of a portion of a human vascular system depicting an abdominal aortic aneurysm and associated aneurysms of the left and right common iliac arteries.

Referring to FIG. 1, the abdominal aortic arch 100 of the human vascular system is shown. The arch includes the abdominal aorta 102 and the right and left common iliac arteries 104 and 104', respectively. In a diseased state, aneurysmal sacs form around these structures, resulting in abdominal aortic aneurysm 106 and aneurysms 108 and 108' of the right and left common iliac arteries, respectively, as illustrated in FIG. 2.

Figure 3:
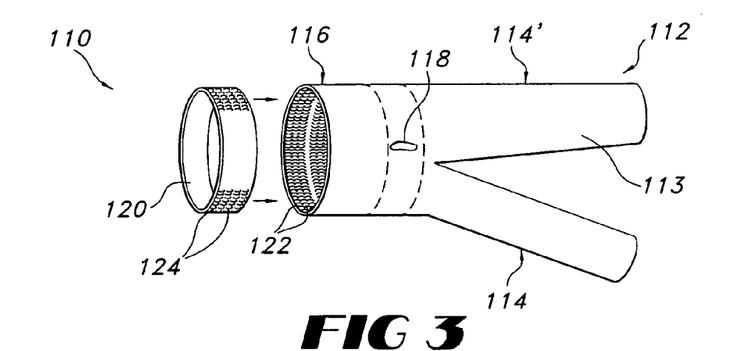
FIG. 3 shows an abdominal aortic stent-graft and patch therefore.

Referring to FIG. 3, a prosthesis 110 of the present invention is shown. Prosthesis 110 includes an endovascular member 112 (e.g., a stent-graft) which is capable of being positioned within the lumen of the abdominal aortic arch 100 for the repair of aneurysms 106, 108, and 108'. As is known in the art, member 112 may include a stent (not shown) and a graft 113 which is supported by the stent. Member 112 includes limbs 114 and 114' for placement into right common iliac artery 104 and left common iliac artery 104', respectively, and includes a trunk 116 for placement into the abdominal aorta 102. Member 112, also has a worn area 118 which has been damaged, for example, by the tortuous flow of blood through abdominal aortic arch 100, and is consequently in need of repair.

Any known stent material and structure may be used to form the stent of member 112 of the present invention. For example, the stent may comprise a sinuous wire formed into a tubular configuration and may be made from a shape memory nitinol (nickel titanium) wire, such as that disclosed in U.S. Pat. No. 6,051,020 to Goicoechea at al., incorporated by reference herein. Typically, the stent is annealed while on a mandrel at an elevated temperature such that it will "remember" the configuration in which it was wound. As such, the formed stent may be radially compressed in order to introduce it into a body lumen and maneuver it to the aneurysm where it will be caused to radially expand to its original state, thereby providing a prosthetic endoluminal surface to the diseased blood vessel.

Additionally, any known graft material and structure may be used to form the graft 113 of member 112 of the present invention. For example, materials which promote endothelial tissue growth on and through the graft structure are typically used. Such materials include, for example, polyester, polytetrafluoroethylene, expanded polytetrafluoroethylene and polyurethane, but may be any suitable biocompatible material.

While member 112 is desirably a stent-graft, it may be other intraluminal prosthetic devices which are suitable for use in the present invention. Additionally, while member 112 shown in FIGS. 3–10 is tubular-shaped, this is representative only and other configurations are possible.

Figure 6:
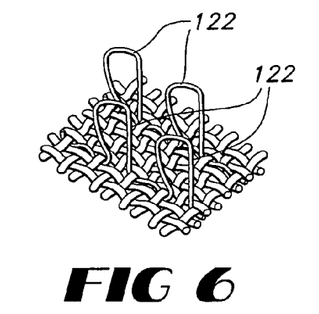
FIG. 6 shows a detailed view of a loop structure used in the present invention.

Member 112 of the present invention includes a hook or loop structure which is complementary with a hook or loop structure of a patch 120 to be attached thereto. For example, as shown in FIG. 3, member 112 has loops 122 on the inner surface thereof. Loops 122, illustrated in greater detail in FIG. 6, are formed from a woven or knitted graft material by velouring of the material or of a second material associated therewith. Loops 122 are desirably formed from polypropylene, polyethylene teraphthalate, polyurethane or from a copolyester elastomer, such as that sold under the tradename Hytrel® by E.I. Du Pont de Nemours and Company. Additionally, loops 122 may be formed from any biocompatible material, including nylon or any suitable synthetic polyester fiber, such as Dacron®. Loops 122 may be provided as a tape which is affixed to the stent and/or graft 113.

Figure 5:
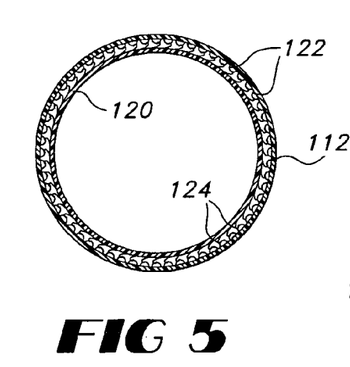
FIG. 5 shows a hook and loop structure of the present invention wherein the hooks are matingly engaged with the loops.

As shown in FIG. 3, member 112 may include a damaged area 118 which is consequently in need of repair. Damaged area 118 results, for example, from the tortuous flow of blood through the lumen of member 112. A patch 120 for the repair of damaged area 118 has hooks 124 on the exterior surface thereof, which may also be in the form of a tape. Hooks 124 are capable of matingly engaging loops 122, as shown in FIG. 5, forming a substantially fluid-tight seal between patch 120 and member 112 at damaged area 118. Hooks 124 and loops 122 may be present on either of the mating elements, it is necessary only that the structures being joined have complementary hook and loop structures.

Figure 4:
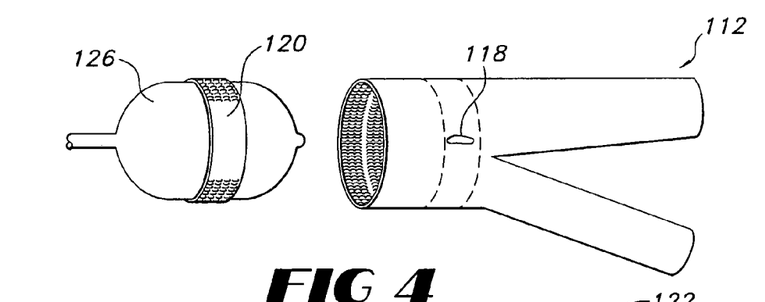
FIG. 4 shows the in situ deployment of the patch shown in FIG. 3.

As shown in FIG. 4, a deployment mechanism 126, such as a balloon catheter, is used to introduce patch 120 in a radially compressed state to damaged area 118 using a minimally-invasive endovascular technique, for example, angioplastic techniques. Once delivery device 126 has been maneuvered to align patch 120 with damaged area 118, patch 120 is caused to radially expand causing hooks 124 present thereon to engage loops 122 of member 112.

Figure 7:
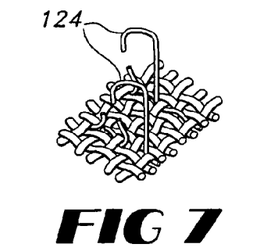
FIG. 7 shows a detailed view of a hook structure used in the present invention.

Hooks 124, shown in greater detail in FIG. 7, may be formed from any biocompatible, textile or thermoplastic material. When formed as a tape, hooks 124 can be any suitable fabric-backed microhoop strip. For example, hooks 124 may be formed from any of the aforementioned materials from which loops 122 may be formed from, including, but not limited to, Nylon®, polypropylene, polyethylene, Dacron®, or molded polyethylene terepthalate. Hooks 124 may be formed from a tape which is affixed to a prosthetic member, or may be incorporated into a material of such a member, for example, into a woven material.

Hooks 124 may be made accordingly to any number of known processes. For example, they may be formed by cutting loops 122, as shown in FIG. 7, or by applying heat to an aforementioned thermoplastic material while simultaneously blowing the material in such a manner as to form a hook structure.

Figure 8:
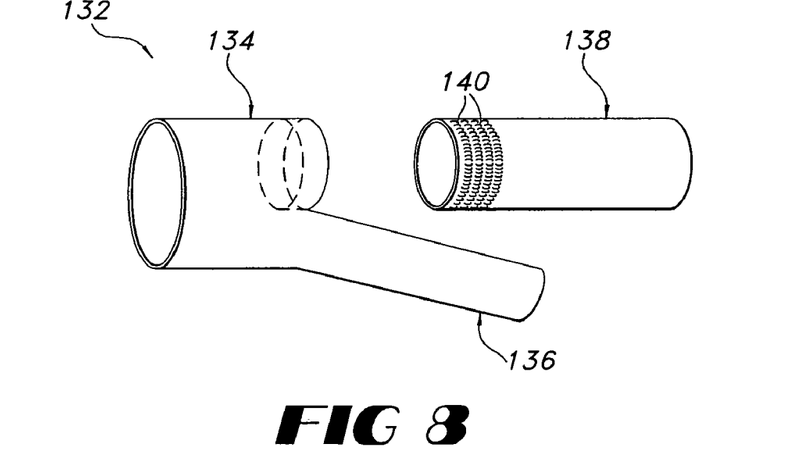
FIG. 8 shows an endovascular prosthesis of the present invention which includes two stent-graft components having hook and loop structures.
Figure 9:
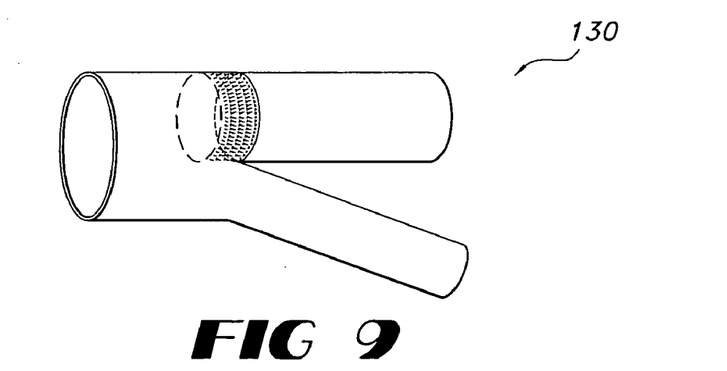
FIG. 9 shows the endovascular prosthesis of FIG. 8 with the stent-graft components matingly engaged through the attachment of the hooks and loops.
Figure 10:
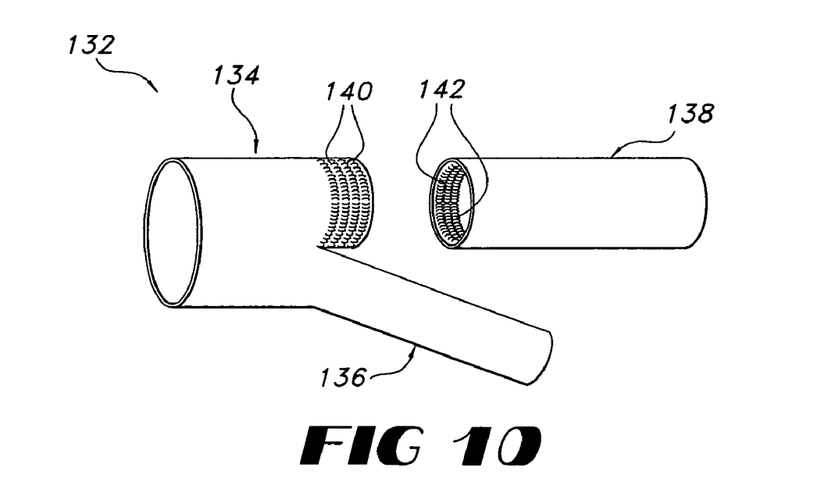
FIG. 10 shows an endovascular prosthesis of the present invention which includes two stent-graft components having hook and loop structures in an arrangement opposite that shown in FIG. 8.

Turning to FIGS. 8, 9 and 10, a prosthesis 130 of the present invention is shown. Prosthesis 130 includes a main stent-graft 132, which comprises the trunk 134 and right limb 136 of prosthesis 130, and includes a branch stent-graft 138, which, when attached to main stent-graft 132, comprises the left limb of prosthesis 130. Hooks 140 and loops 142 of the aforementioned materials and structures are present on main stent-graft 132 and branch stent-graft 138, as shown in FIGS. 8 and 10, thereby permitting these elements to be joined in fluid-tight engagement, as shown in FIG. 9 and as will be described in fuller detail below with reference to the Example.

Examples of multiple-component bifurcated stents and methods of introducing such stents to aneurysms useful in the present invention are described in U.S. Pat. Nos. 5,716,365, 5,683,450, 5,718,724, 5,776,180, 5,938,696, 5,916,263, and 6,051,020, all to Goicoechea et al., all of which are incorporated herein by reference.

EXAMPLE

In Situ Stent-Graft Deployment

For purposes of the present example, the term "proximal" refers to a position nearest the heart and the term "distal" refers to a position furthest from the heart. As shown in FIG. 1, the abdominal aorta 102 extends caudally to the common iliac arteries 104 and 104', which branch to the right and left, respectively. Each common iliac artery branches to an external iliac artery (not shown) which becomes the femoral artery (not shown) below the inguinal ligament (not shown).

Incisions (not shown) are made which expose the common femoral arteries on the right and left sides. A conventional angiographic guidewire (not shown) is inserted into the incised left femoral artery. The guidewire is advanced until its distal end is above the aneurysm within the vasculature. Typically, the guidewire is at least 0.025 inches in diameter and is composed of tempered stainless steel which is covered with a synthetic material, such as TEFLON®. The guidewire typically remains in a fixed position throughout the endoluminal procedure.

An introducer (not shown), which supports branch stent-graft 138, having an interior surface of loops 142, as shown in FIG. 10, is then inserted into the vasculature and over the guidewire where it is maneuvered to the left common iliac artery 104' below the aneurysm. An example of an introducer which may be used in the present invention is that shown in U.S. Pat. No. 5,683,450, to Goicoechea et al. A balloon catheter (not shown) is then extended while maintaining the outer sheath of the introducer in a fixed position in order to position the balloon above the renal arteries.

The introducer is then positioned to place branch stent-graft 138 within the left common iliac artery 104'. Proper placement may be facilitated with the use of radiopaque markers. Once the introducer is properly positioned, the balloon is inflated to occlude the aorta.

The outer sheath of the introducer is then withdrawn until the proximal end of branch stent-graft 138 emerges from the outer sheath. Using a radiopaque marker disposed on the proximal end of the prosthesis, the introducer is maneuvered until precise positioning of branch stent-graft 138 within the left common iliac artery is obtained. Once branch stent-graft 138 has been properly positioned, the outer sheath of the introducer is fully withdrawn, allowing branch stent-graft 138 to radially expand, thereby contacting the endoluminal surface of the left common iliac artery 104'.

Once branch stent-graft 138 has been properly positioned, the balloon is deflated and drawn into the lumen of branch stent-graft 138, where it may be inflated to further secure branch stent-graft 138 to the endoluminal wall of the left common iliac artery 104'. The balloon is then deflated and maintained within the lumen of branch stent-graft 138 where it will be used to secure main stent-graft 132 thereto. Additionally, the introducer may be withdrawn from the vasculature, leaving the guidewire in place.

Main stent-graft 132, having an external structure of hooks, is then deployed to the aneurysm. Main stent-graft 132 includes trunk 134 and a right limb 136. Hooks 140 on the exterior surface of trunk 134 are capable of complementary engagement with loops 142 on the interior surface of branch stent-graft 138. A guidewire (not shown) is inserted into the incised right femoral artery and advanced until its distal end is above the aneurysm within the vasculature. An introducer (not shown) which includes main stent-graft 132 is then inserted into the vasculature and over the guidewire where it is maneuvered to the right common iliac artery 104 below the aneurysm.

Once in the aorta, the introducer is positioned such that the proximal end of its outer sheath is approximately level with the renal arteries. A balloon catheter (not shown) is then extended while maintaining the outer sheath of the introducer in a fixed position such that the balloon is positioned above the renal arteries. The introducer is then positioned to place trunk 134 in the desired deployment location, which may be facilitated with the use of radiopaque markers. Once the introducer is properly positioned, the balloon is inflated to occlude the aorta.

The outer sheath of the introducer is then withdrawn until the proximal end of first stent-graft 132 emerges from the outer sheath. Using a radiopaque marker disposed on the proximal end and/or distal ends of main stent-graft 132, the introducer is rotated until proper alignment of the main stent-graft 132 and branch stent-graft 138 is obtained, such that hooks 140 of main stent-graft 132 align with loops 142 of branch stent-graft 138 such that there is sufficient overlap between the first and second stent grafts to ensure that a substantially fluid tight seal will form therebetween. Once properly positioned, the outer sheath of the introducer is withdrawn sufficiently as to cause trunk 134 to radially expand and contact the endoluminal surface of the abdominal aorta while also causing hooks 140 to engage loops 142. The outer sheath of the introducer is then further withdrawn to deploy right limb 136 of main stent-graft 132 within the right common iliac artery 104, such that it radially expands it contacts the endoluminal surface thereof.

The deflated balloon contained within the lumen of branch stent-graft 132 may then be inflated to provide a force against the inner surface of main stent-graft 132 at the point where hooks 140 present on the exterior surface thereof engage loops 142 on the interior surface of branch stent-graft 138, thereby securing hooks 140 to loops 142, ensuring that a substantially fluid tight seal is created therebetween. Both balloons are then deflated to allow blood to flow through the thus-assembled bifurcated prosthesis 130, shown in FIG. 9, such that main stent-graft 132 partially overlays branch stent-graft 138 at the point where hooks 140 and loops 142 engage one another, thereby providing a cuff which promotes the fluid tight characteristic of assembled stent-graft 130.

Alternatively, the above procedure may be performed such that main stent-graft 132 is deployed at the aneurysm prior to deployment of branch stent-graft 138, such that a hook or loop structure on main stent-graft 132 will engage a hook or loop structure on branch stent graft 138, which is positioned partially inside of main stent-graft 132 such that there is an overlap therebetween. Additionally, either main stent-graft 132 or branch stent-graft 138 may have either of hooks 140 or loops 142 thereon, so long as the stent-grafts are mated in a complementary manner when engaged with one another. It will further be appreciated that main stent-graft 132 and branch stent-graft 138 may be shaped to facilitate alignment and mating therebetween, for example, main stent-graft 132 may be a frustoconical member adapted for engaging branch stent-graft 138, also a frustoconical member.

While the invention has been illustrated and described herein in terms of its use as an endoprosthesis for treating an aneurysm, it will be apparent to those skilled in the art that the prosthesis can be used in other instances in other vessels of the body. Further, while stent-grafts have been described for use in the present invention, grafts and stents alone may also be used in the present invention.

What is claimed is:

1. A method of repairing a damaged area of an endovascular prosthesis having a hook or loop structure and which is positioned within a body lumen, comprising the step of:
    attaching a patch to a tubular endovascular prosthesis, said endovascular prosthesis including a damaged area, wherein said patch has a hook or loop structure cooperative with a hook or loop structure of said endovascular member for maintaining said patch in substantially fluid tight communication with said endovascular member;
    wherein said patch covers said damaged area of said endovascular prosthesis; and
    wherein said tubular endovascular prosthesis is selected from the group consisting of grafts, stents and stent-grafts.

2. The method of claim 1, further comprising the step of delivering said patch to said endovascular member through a body lumen containing said endovascular member.

3. The method of claim 1, wherein said patch comprises one of a hook structure and a loop structure and said endovascular member comprises the other of said hook structure and said loop structure.

4. The method of claim 1, wherein said attaching step occurs in situ.

5. The method of claim 1, wherein said attaching step is effected by expanding a balloon affixed to a catheter to cause said hook or loop structure of said patch to engage the other of said hook or loop structure of said endovascular member.

6. The method of claim 2, wherein said delivery step is effected by use of a catheter.

7. The method of claim 2, wherein said delivery step is effected by use of a balloon catheter.

* * * * *

UNITED STATES PATENT AND TRADEMARK OFFICE
CERTIFICATE OF CORRECTION

PATENT NO. : 6,986,786 B1
DATED : January 17, 2006
INVENTOR(S) : J. Smith

It is certified that error appears in the above-identified patent and that said Letters Patent is hereby corrected as shown below:

Column 2,
Line 40, should read -- ...resulting from the tendency... --.

Column 5,
Line 57, should read -- ...where prostheses are susceptible... --.

Column 9,
Lines 8-9, should read -- ...such that it radially expands when it contacts... --.

Signed and Sealed this

Twenty-eighth Day of March, 2006

JON W. DUDAS
*Director of the United States Patent and Trademark Office*